United States Patent [19]

Buzza et al.

[11] 4,149,949

[45] Apr. 17, 1979

[54] ELECTROCHEMICAL ANALYSIS APPARATUS EMPLOYING SINGLE ION MEASURING SENSOR

[75] Inventors: Edmund E. Buzza, Fullerton; John E. Lillig, Diamond Bar, both of Calif.

[73] Assignee: Beckman Instruments, Inc., Fullerton, Calif.

[21] Appl. No.: 922,459

[22] Filed: Jul. 6, 1978

[51] Int. Cl.² ............................................. G01N 27/26
[52] U.S. Cl. .................................................. 204/195 P
[58] Field of Search ............................ 204/195 P, 1 H

[56] References Cited

U.S. PATENT DOCUMENTS

| | | | |
|---|---|---|---|
| 3,857,771 | 12/1974 | Sternberg | 204/195 B |
| 3,869,354 | 3/1975 | Montalvo | 204/195 P |

*Primary Examiner*—Howard S. Williams

*Attorney, Agent, or Firm*—R. J. Steinmeyer; Robert R. Meads; John R. Shewmaker

[57] ABSTRACT

Apparatus for measuring $CO_2$ in serum with a single pH sensor of the electrolyte flow-through type, the sensor including a gas-permeable membrane selectively passing $CO_2$ into an electrolyte filled space adjacent a pH sensing electrode for reacting with the electrolyte to produce a pH change therein. The electrolyte space is connected by a conduit to an electrolyte reservoir for flowing fresh electrolyte to and through the electrolyte space prior to a sample measurement. A stainless steel metal electrode directly contacts the electrolyte of constant composition in the conduit upstream of the pH sensor to derive a reference potential thereat. The potential across the pH sensor and the stainless steel electrode is monitored, differentiated, and the maximum value of the differentiated signal measured to determine the $CO_2$ concentration.

5 Claims, 2 Drawing Figures

ELECTROCHEMICAL ANALYSIS APPARATUS EMPLOYING SINGLE ION MEASURING SENSOR

BACKGROUND OF THE INVENTION

1. Field of the Invention

The present invention relates generally to electrochemical measuring apparatus and, more particularly, to apparatus for measuring ionic species in solution. The apparatus is particularly advantageous for measuring a substance reactable with an electrolyte by monitoring a change in ion concentration of the electrolyte when reacted with the substance.

2. Description of the Prior Art

U.S. Pat. No. 4,003,705, assigned to the assignee of the present invention, describes an electrochemical analysis apparatus for measuring carbon dioxide in serum employing a common solution ground and a pair of electrolyte flow-through pH sensors having respective electrolyte chambers connected in series for flowing fresh electrolyte to each chamber prior to sample measurement. The serum sample is reacted with an acid reagent in a sample chamber to release carbon dioxide which diffuses through a gas-permeable membrane into the electrolyte space of one of the pH sensors to react with the electrolyte therein. Upon reacting with the carbon dioxide, the electrolyte undergoes a change in pH. By contrast, the second pH sensor and solution ground is located in the series electrolyte flow path remote from the first sensor and is not exposed to the carbon dioxide. The outputs of the respective pH sensors are connected to first and second high impedance inputs of a differential amplifier to derive a differential pH signal at the amplifier output. The differential pH signal, in turn, is differentiated to provide an output signal the maximum value of which provides a measure of the carbon dioxide content in the sample.

While the foregoing apparatus represents an advance in the art of electrochemical analysis, it does so with a moderate degree of electronic and mechanical hardware. That is, a pair of pH sensors, each comprising a standard glass pH measuring electrode, are utilized to develop the differential pH signal, and the noted differential amplifier is employed for processing the signal. Accordingly, it would be desirable to achieve the foregoing electrochemical measurements with an arrangement of reduced electronic and mechanical complexity.

SUMMARY OF THE INVENTION

The present invention resides in a simplified electrochemical analysis apparatus for measuring a substance reactable with an electrolyte by means of an ion measuring sensor of the electrolyte flow-through type without sacrificing the degree of accuracy and reliability required of such apparatus in a clinical setting. To these ends, applicants have discovered that the combination of (1) a single ion measuring sensor of the electrolyte flow-through type including an electrolyte space connected in an electrolyte flow path of constant composition and (2) a metal contact in the flow path remote from the sensor electrolyte space may be employed to derive a pH signal upon reaction of a substance selectively passed into the electrolyte space of the sensor. In the preferred embodiment it has been found that a piece of stainless steel contacting the electrolyte upstream of the sensor provides a stable reference potential thereat against which the potential of the ion measuring sensor, during the substance-electrolyte reaction therein, may be compared. Circuit means is connected across the output of the ion measuring sensor and the metal contact to develop solely from the potential difference therebetween an output signal indicative of the concentration of the substance monitored by the sensor. The output signal is differentiated and the maximum value of the differentiated signal measured to derive a measure of the substance. In this manner a single ion measuring sensor, the output of which is connected to a single ended amplifier, is employed for sample measurement thereby reducing the electrical and mechanical complexity of the prior apparatus.

DESCRIPTION OF THE PREFERRED EMBODIMENT

Figure 1:
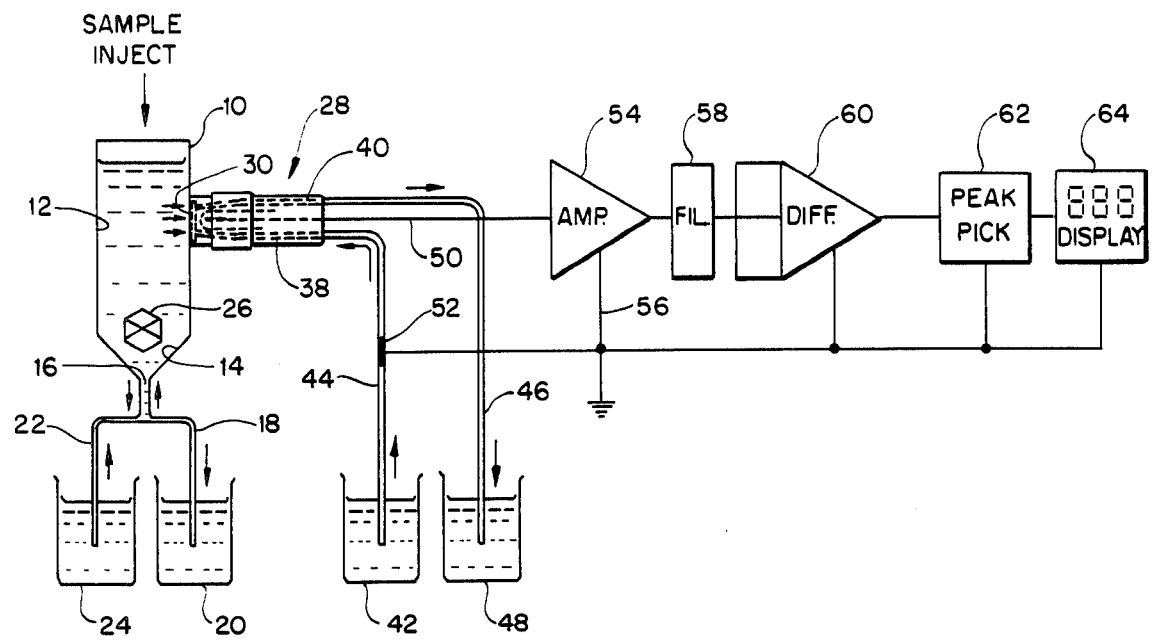
FIG. 1 is a combined diagrammatic and electrical schematic diagram of a preferred form of the electrochemical apparatus of the invention.

The drawing figure illustrates an electrochemical analysis apparatus of the invention as adapted to apparatus of the type described in aforementioned U.S. Pat. No. 4,003,705. As such, the present embodiment incorporates many of the same mechanical and electrical components of the prior system, and for this reason the various features will be described only to the extent necessary for an understanding of the present invention. Specific reference should be made to the prior patent for additional details regarding structure and operation of the common features.

Figure 2:
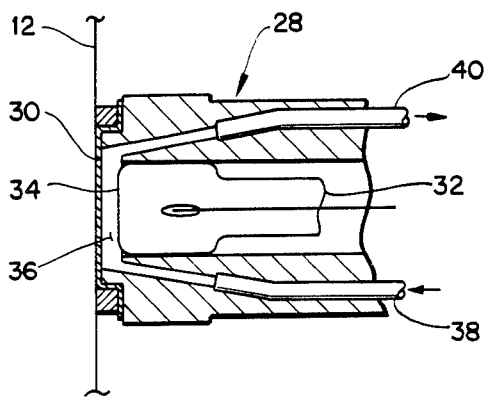
FIG. 2 is an exploded, fragmentary view, taken in a generally vertical plane through the ion measuring sensor employed in the FIG. 1 apparatus.

The analysis apparatus as illustrated includes an analysis cell 10 defining a vertically extending chamber 12 having an open upper end through which a sample, such as serum, to be analyzed is injected into the chamber by means of a pipette or the like. The bottom 14 of the chamber is formed in the shape of an inverted cone with an open passage 16 formed at the apex thereof. Passage 16 is connected by a first conduit 18 to a reservoir 20 of acid reagent, such as sulfuric acid. Passage 16 is also connected through a second conduit 22 to a waste reservoir 24. With this arrangement, a pump (not shown) pumps acid reagent from reservoir 20 into measuring chamber 12 through conduit 18 and passage 16 prior to an analysis operation. Similarly, after an analysis operation, a pump (not shown) pumps the contents of the chamber to waste through passage 16 and conduit 22. A conventional magnetic stirring element 26 is provided in the chamber and is rotated in a conventional manner for stirring the contents of the chamber. As noted, a serum sample introduced into chamber 12 reacts with the acid reagent therein liberating carbon dioxide in the process. In order to measure the sample carbon dioxide, an electrolyte flow-through, ion measuring sensor, indicated generally by numeral 28, communicates with the contents of the chamber 12 through a barrier 30 which is selectively permeable to carbon dioxide. Suitable materials for barrier 26 are membranes formed of silicon rubber, polyethylene, or polytetrafluoroethylene. Sensor 28 may be identical in construction to the sensor described in the aforementioned patent. Briefly, as most clearly illustrated in FIG. 2, it comprises a conventional pH sensing electrode 32 having a pH sensitive glass surface 34. A chamber or space 36 for electrolyte is defined between the surface of ion sensitive glass 34 and barrier 30. A pair of stainless steel tubes 38 and 40 extend longitudinally within the sensor and are in fluid communication with opposite sides of the electrolyte space 36. Tube 38 is connected to a reservoir 42 of alkaline electrolyte, such as potassium bicarbonate, by a conduit 44. Tube 40 is connected by a conduit 46 to a waste receptacle 48. Thus arranged, the alkaline electrolyte is adapted to be pumped from reservoir 42 by a pump (not shown) through conduit 44 and tube 38 into and through electrolyte space 36 and out through tube 40 and conduit 46 toward waste 48. In this manner electrolyte in space 36 may be purged prior to a sample measurement and replaced with fresh electrolyte.

With the foregoing arrangement, pH sensor 28 operates by monitoring the pH of the electrolyte in electrolyte space 32 and supplying a signal on output conductor 50 indicative thereof. Carbon dioxide liberated by the sample-acid reagent reaction in chamber 12 passes into the electrolyte space 36 through barrier 30 and reacts with the alkaline electrolyte therein changing the pH thereof. The degree of pH change is employed to derive a measure of the carbon dioxide.

Applicants have discovered that a pH signal providing an accurate measure of carbon dioxide or other measured substance may be derived between the output of one ion sensor 28 and a metal contact 52 in the electrolyte flow path remote from the sensor. Specifically, a stainless steel tube 52, approximately one inch in length and 0.03 inches in internal diameter immersed in the electrolyte at a location of constant electrolyte composition remote from the sensor, such as upstream thereof, has been found to provide a stable reference potential unaffected by the carbon dioxide induced pH change in electrolyte space 32 and hence against which the pH change may be measured. For this purpose the output conductor of pH sensor 28 is connected to the input of a conventional single-ended amplifier 54, and the amplifier is referenced to ground by a conductor 56 to the stainless steel contact 52. Thus arranged, the potential supplied to the input of amplifier 54 corresponds to the difference in pH, if any, between electrolyte in electrolyte space 36 and electrolyte upstream thereof at at contact 52.

The output of amplifier 54 is connected through a conventional low pass filter 58 to differentiator circuit 60 which differentiates and further amplifies the pH signal from amplifier 52 to derive a signal at its output proportional to the instantaneous time rate of change of pH. In addition, the differentiator blocks any d.c. offset voltage present at the output of amplifier 54. The output of differentiator circuit 60, in turn, is connected to a peak pick and hold amplifier 62 which senses a maximum value of the time rate of change signal and supplies such to a display 64 for readout. The differentiator 60, amplifier 62, and display 64 may be identical to those of aforementioned U.S. Pat. No. 4,003,705.

The foregoing arrangement monitors electrolyte pH in electrolyte chamber 36 as compared with electrolyte pH at reference contact 52 and monitors the change in pH induced by introduction of $CO_2$ into the electrolyte chamber. Ideally the potential difference between sensor 28 and reference contact 52 should be near zero prior to sample introduction and such was achieved in the prior arrangement between the two pH sensors 24 there employed. In the present arrangement it is possible for a constant offset voltage to exist between reference contact 52 and ion sensor 28. However, this constant offset is effectively removed by electronic biasing and/or by differentiator circuit 48 since the derivative of a constant is zero. Consequently, any constant offset coupled to the input of differentiator 58 is not translated to its output and thus the differentiator output corresponds to that of the prior system. With the present arrangement the common mode noise rejection is not retained. However, it has been found that (1) constant offsets are rejected by the differentiator as noted above and (2) all other common mode signals, if present, are of such a high frequency content (greater than 10 Hz., e.g. 60 Hz.) that they can be rejected by low pass filter 58. The present system, like the prior, is temperature sensitive and requires that the temperature of the acid reagent, the alkaline electrolyte and the measuring sensors associated therewith be maintained as nearly constant in temperature as possible.

From the foregoing it will be evident that the present invention enables measurement of a substance, such as $CO_2$ in serum, by reacting the substance with the electrolyte of an electrolyte flow-through ion measuring sensor using only one such sensor while establishing a reference potential therefor by means of a metal reference contact directly contacting the electrolyte flowed through the sensor at a location in the electrolyte flow path upstream of the sensor. The arrangement retains all of the desirable features of prior arrangements, but eliminates one pH measuring sensor and a high input impedance differential amplifier without sacrificing the degree of accuracy and reliability required of commercial grade instruments for measuring the physiological and pathological condition of patients. Moreover, it will be apparent that the present invention may be adapted to the measurement of gases, either acidic or basic, other than carbon dioxide by including flow-through electrolytes reactive with such gases and associated ion measuring sensors for measuring pH or other ionic specie which change in concentration upon reaction of the electrolyte and the gas. Moreover, while a preferred embodiment of the invention has been illustrated and described, it will be apparent that modifications may be made therein without departing from the spirit and scope of the invention as defined in the appended claims.

What is claimed is:

1. Electrochemical analysis apparatus for measuring a substance reactable with an electrolyte by measuring a change in concentration of an ionic species in said electrolyte upon reacting said substance and said electrolyte comprising:

an ion measuring sensor including an ion sensing surface, means for generating an output potential related to the ionic species concentration sensed thereby, an electrolyte space defined adjacent said ion sensing surface, means for passing electrolyte containing said ionic species into and out of said electrolyte space in contact with said ion sensing surface, and means selectively permeable to said substance to be measured for admitting said substance into said electrolyte space for reaction with said electrolyte therein, said ion measuring sensor monitoring any change in the concentration of said ionic species resulting from said reaction;

means defining an electrolyte flow path connected to said electrolyte space for conveying electrolyte thereto;

a metal reference contact in said electrolyte flow path contacting said electrolyte therein remote from said electrolyte space for deriving a reference potential thereat; and circuit means having a single input terminal and a ground terminal connected, respectively, to the output of said ion measuring sensor and to said metal reference contact for developing solely from the potential difference therebetween an output signal indicative of the concentration of said substance upon reaction thereof with said electrolyte in said electrolyte space.

2. The apparatus of claim 1 wherein said circuit means includes means for developing the first derivative of said output signal, and means for measuring a maximum of the first derivative signal.

3. The apparatus of claim 1 further including low pass filter means for rejecting high frequency components of said output signal.

4. The apparatus of claim 2 wherein the ion measuring sensor is a pH sensor.

5. The apparatus of claim 1 wherein said metal reference contact is stainless steel contacting said electrolyte.

* * * * *